United States Patent
Yamada et al.

(10) Patent No.: US 11,609,238 B2
(45) Date of Patent: Mar. 21, 2023

(54) METHOD FOR DETECTING A RADICAL COMPOUND DERIVED FROM A LIPID AND A COMPOUND DERIVED FROM THE RADICAL COMPOUND

(71) Applicants: Ken-ichi Yamada, Fukuoka (JP); FUSO PHARMACEUTICAL INDUSTRIES, LTD., Osaka (JP)

(72) Inventors: Ken-ichi Yamada, Fukuoka (JP); Yuta Matsuoka, Fukuoka (JP); Keiichi Yamamoto, Osaka (JP)

(73) Assignees: KEN-ICHI YAMADA, Fukuoka (JP); FUSO PHARMACEUTICAL INDUSTRIES, LTD., Osaka (JP)

( * ) Notice: Subject to any disclaimer, the term of this patent is extended or adjusted under 35 U.S.C. 154(b) by 1280 days.

(21) Appl. No.: 15/965,096

(22) Filed: Apr. 27, 2018

(65) Prior Publication Data

US 2018/0328951 A1    Nov. 15, 2018

(30) Foreign Application Priority Data

Apr. 28, 2017 (JP) .............................. JP2017-090739

(51) Int. Cl.
| | |
|---|---|
| *C07D 413/12* | (2006.01) |
| *G01N 33/92* | (2006.01) |
| *C11C 1/00* | (2006.01) |
| *G01N 33/58* | (2006.01) |

(Continued)

(52) U.S. Cl.
CPC .......... *G01N 33/92* (2013.01); *C07D 413/12* (2013.01); *C11B 1/10* (2013.01); *C11C 1/002* (2013.01); *G01N 33/582* (2013.01); *C07D 271/12* (2013.01)

(58) Field of Classification Search
CPC .... C07D 413/12; C07D 271/12; G01N 33/92; G01N 33/582; C11B 1/10; C11C 1/002
See application file for complete search history.

(56) References Cited

U.S. PATENT DOCUMENTS

| | | |
|---|---|---|
| 2014/0273055 A1 | 9/2014 | Kerr et al. |
| 2018/0328951 A1 | 11/2018 | Yamada et al. |

FOREIGN PATENT DOCUMENTS

| | | |
|---|---|---|
| JP | 2008-164554 | 7/2008 |
| JP | 2009-108037 | 5/2009 |
| JP | 2012-225762 | 11/2012 |

(Continued)

OTHER PUBLICATIONS

Wang et al. A reversible fluorescence probe for detection of ClO-/AA redox cycle in aqueous solution and in living cells. (Year: 2016).*

(Continued)

*Primary Examiner* — Shafiqul Haq
(74) *Attorney, Agent, or Firm* — Hamre, Schumann, Mueller & Larson, P.C.

(57) ABSTRACT

[Problem] To provide a method of scavenging an unstable radical derived from a lipid and analyzing structures of those radicals.
[Means for solution] A fluorescent nitroxide (NBD-Pen) is made to act to scavenge a lipid radical or a fragment radical thereof, and fluorescent detection liquid chromatography (LC/FL) and mass spectrometry (MS) are combined to identify lipid-derived radicals contained in a lipid extract.

2 Claims, 11 Drawing Sheets

(51) Int. Cl.
  *C11B 1/10* (2006.01)
  *C07D 271/12* (2006.01)

(56) References Cited

FOREIGN PATENT DOCUMENTS

JP  2016-513795  5/2016
WO  2014/079946  5/2014

OTHER PUBLICATIONS

Yamada K. et al., "Fluorescence probes to detect lipid-derived radicals," Nature Chemical Biology, 2016, vol. 12, pp. 608-613.
Hollyfield et al., Nature Medicine, vol. 14, No. 2, Feb. 2008, pp. 194-198.
Scbutt et al., Investigative Ophthalmology & Visual Science, vol. 44, No. 8, Aug. 2003, pp. 3663-3668.
Verna et al., Pharmacol. Ther., vol. 71, No. 1/2, pp. 57-81, 1996.
Park et al., Cell, 140, pp. 197-208, Jan. 22, 2010.
Maeda et al., Cell, vol. 121, pp. 977-990, Jul. 1, 2005.
"Development of an estimation method on a structure of a lipid radical for targeting a lipid-derived fragment radical", Heisei 28, Nov. 19, 2016, published by Public Interest Corporate Group The Pharmaceutical Society of Japan, Kyushu Branch, with its translation of the abstract.
EPO Office Action corresponding EP Application No. 18791391.8, dated Sep. 28, 2021, 6 pages.
EPO Extended European Search Report for corresponding EP Application No. 18791391.8, dated Aug. 20, 2020, 10 pages.
Timothy J. Lyons, MD, "Glycation and Oxidation: A Role in the Pathogenesis of Atherosclerosis", The American Journal of Cardiology; vol. 71, issue 6, Feb. 25, 1993, pp. B26-B31.
Javadzadeh et al. "Serum Paraoxonase Phenotype Distribution in Exudative Age-Related Macular Degeneration and its relationship to homocysteine and oxidized low-density lipoprotein", The Journal of Retinal and Vitreous Diseases; vol. 32, No. 4, 2012; pp. 658-666.
Cerami et al., "Glucose and Aging", Sci. Am. 256; pp. 82-88 1987.
Itabe et al., "Measurement of Plasma Oxidized Low-Density Lipoprotein and its Clinical Implications", Journal of Atherosclerosis and Thrombosis; vol. 14, No. 1, 2007; pp. 1-11.
International Preliminary Report on Patentability corresponding to Application No. PCT/JP2018/017287 dated Nov. 7, 2019, 14 pages.
Kotani et al., "Distribution of immunoreactive malondialdehyde-modified low-density lipoprotein in human serum", Biochimica et Biophysica Acta 1215 (1994) 121-125.
Saito et al., "Reductions in degree of mineralization and enzymatic collagen cross-links and increases in glycation-induced pentosidine in the femoral neck cortex in cases of femoral neck fracture", Osteoporos international.; 2006, vol. 17: pp. 986-995.
Brownlee et al., "Aminoguanidine Prevents Diabetes-Induced Arterial Wall Protein Cross-Linking", Science. 1986; 232: pp. 1629-1632.
Holvoet et al., "Association of High Coronary Heart Disease Risk Status With Circulating Oxidized LDL in the Well-Functioning Elderly", Arterioscler Thromb Vasc. Biol.; 2003, 23(8). pp. 1444-1448.
Miyata et al., "2-Isoproylidenehydrazone-4-oxo-thiazolidin-5-ylacetanilide (OBP-9195) treatment inhibits the development if intimal thickening after balloon injury if rat carotid artery: role of glycoxidation and lipoxidation reactions in vascular tissue damage", FEBS Letters 445 (1999) pp. 202-206.
Reddy et al., "Involvement of Maillard Reactions in Alzheimer Disease," Neurotoxicity Research, 2002, vol. 4 (3), pp. 191-209.
Non-Final Office Action dated Oct. 1, 2021 issued in U.S. Appl. No. 16/609,028, 25 pages.
Final Office Action dated Apr. 26, 2022 issued in U.S. Appl. No. 16/609,028, 22 pages.
Negre-Salvayre A. et al., "Advanced lipid peroxidation end products in oxidative damage to proteins. Potential role in diseases and therapeutic prospects for the inhibitors," British Journal of Pharmacology, 2008, vol. 153, pp. 6-20.
"About Glycation Stress" Karada Lab. Inc. <URL:https://web.archive.org/web/20161110173212/http://ebn.arkray.co.jp/disciplines/glycation-stress/stress-01/> 5 pages; discussed in the attached Japanese Office Action.
Office Action issued for Japanese Patent Application No. 2019-514675, dated Mar. 29, 2022, 8 pages including machine translation.

* cited by examiner

[Figure 1]
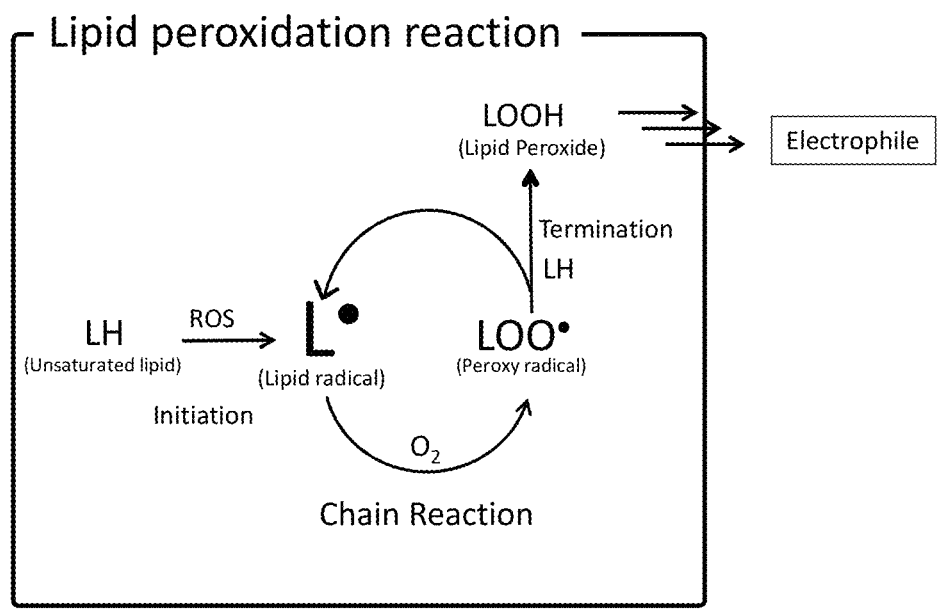

[Figure 2]
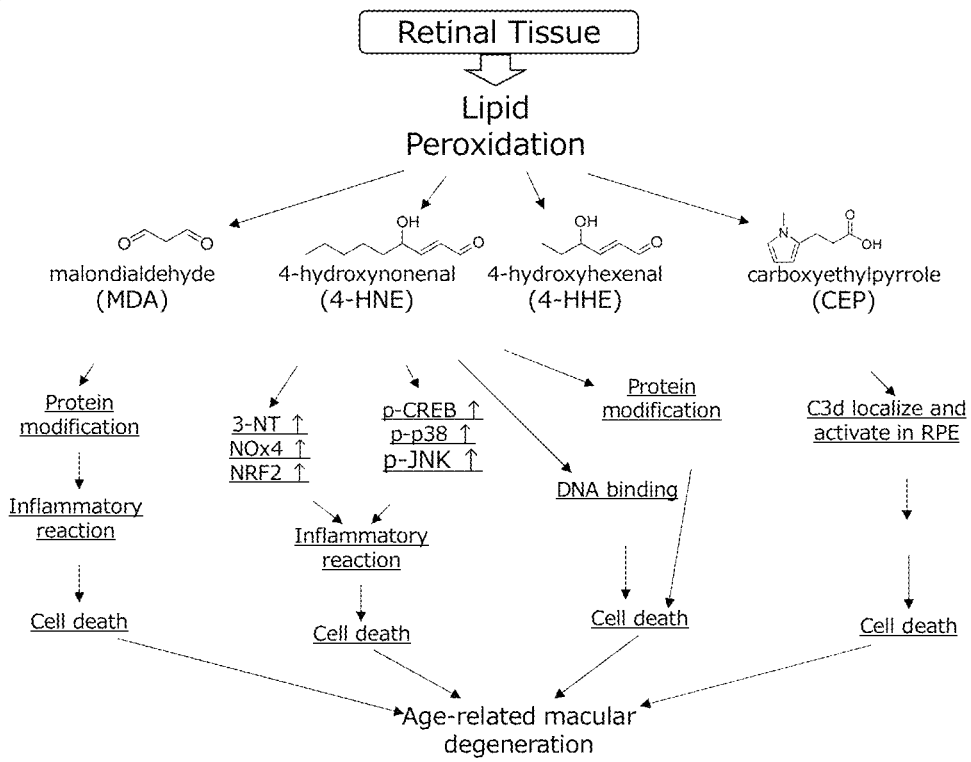

[Figure 3]
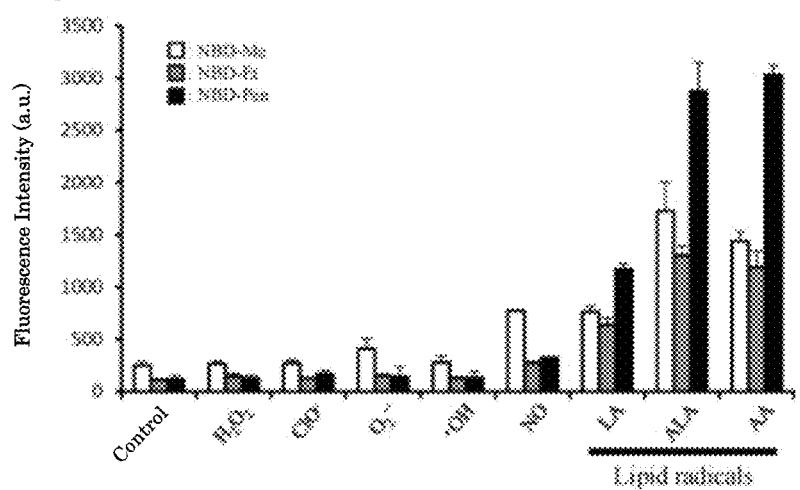

[Figure 4]
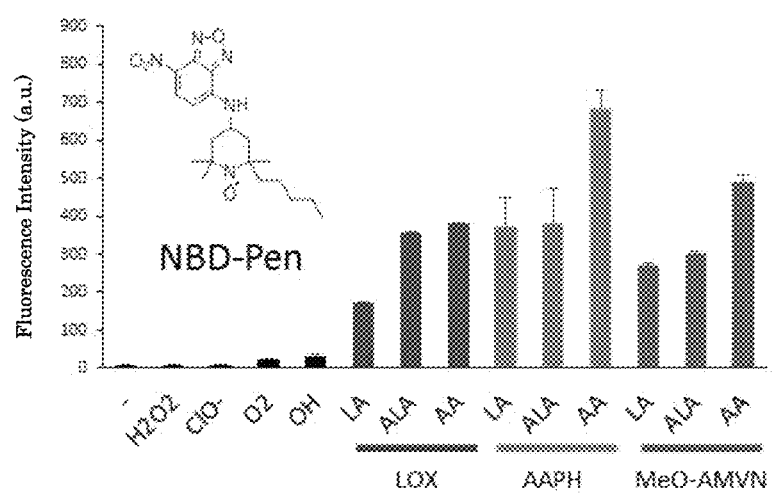

[Figure 5]
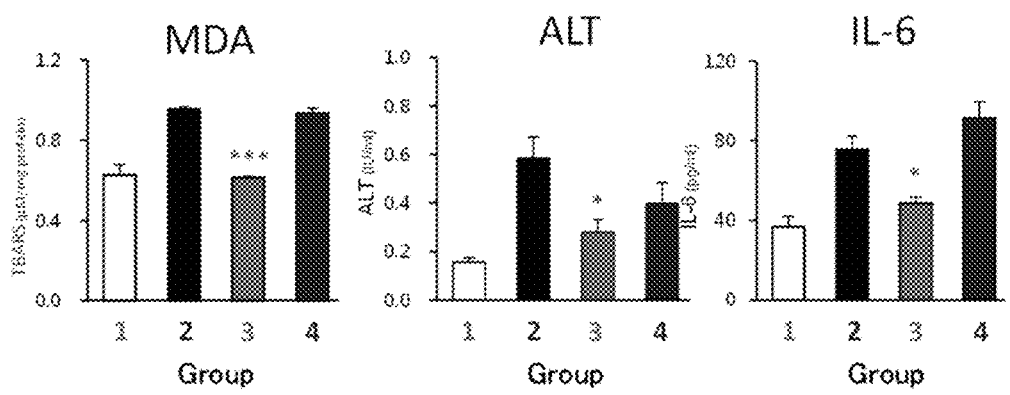

[Figure 6]
(a)
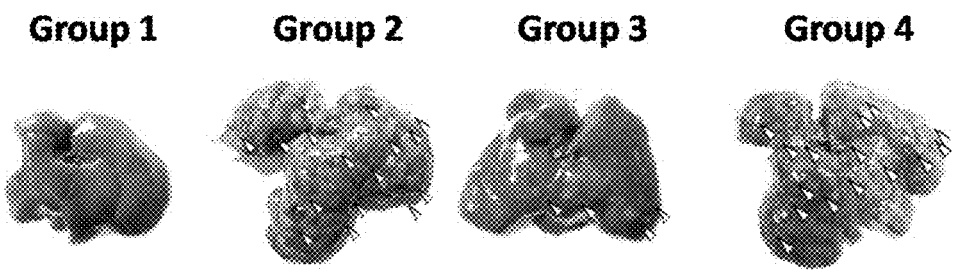
(b)
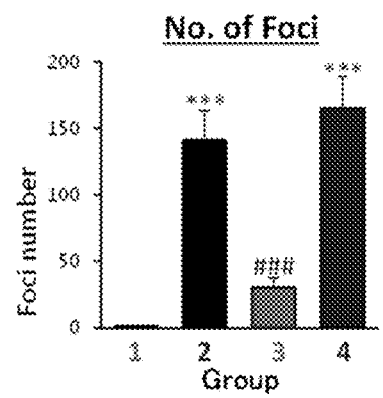
n=8, mean+SEM ***p<0.001. v.s. Control, ###p<0.001 v.s. DEN+Compound(-)

[Figure 7]
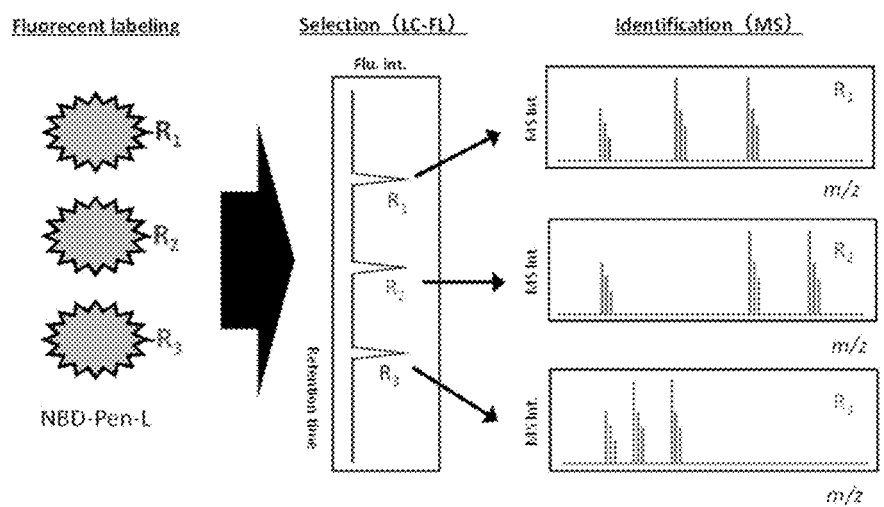

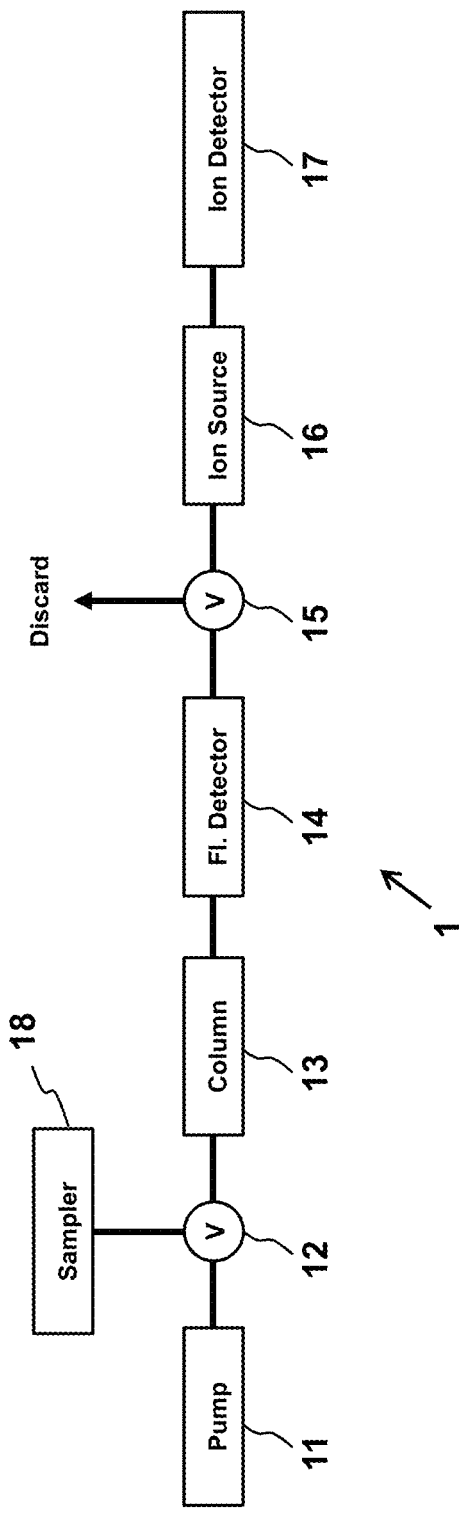
[Figure 8]

[Figure 9]
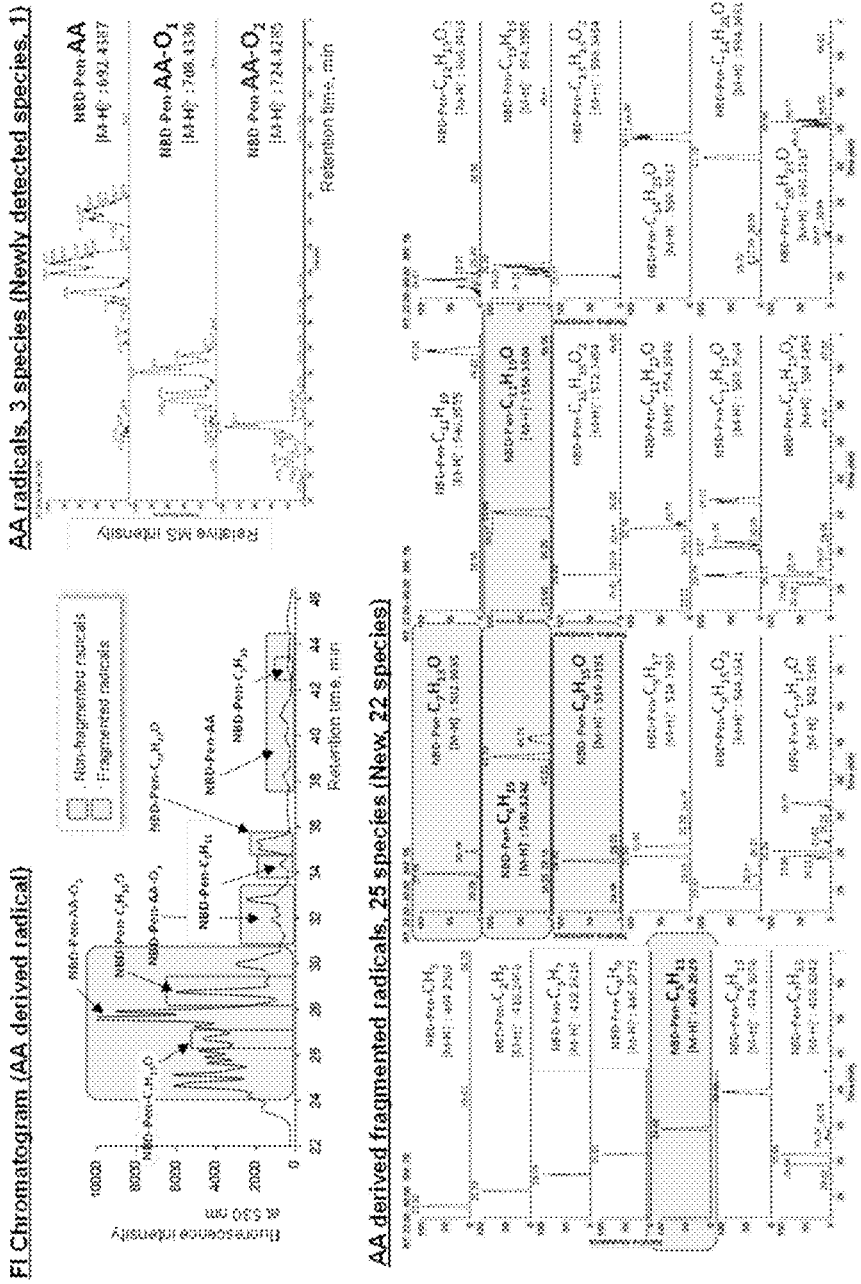

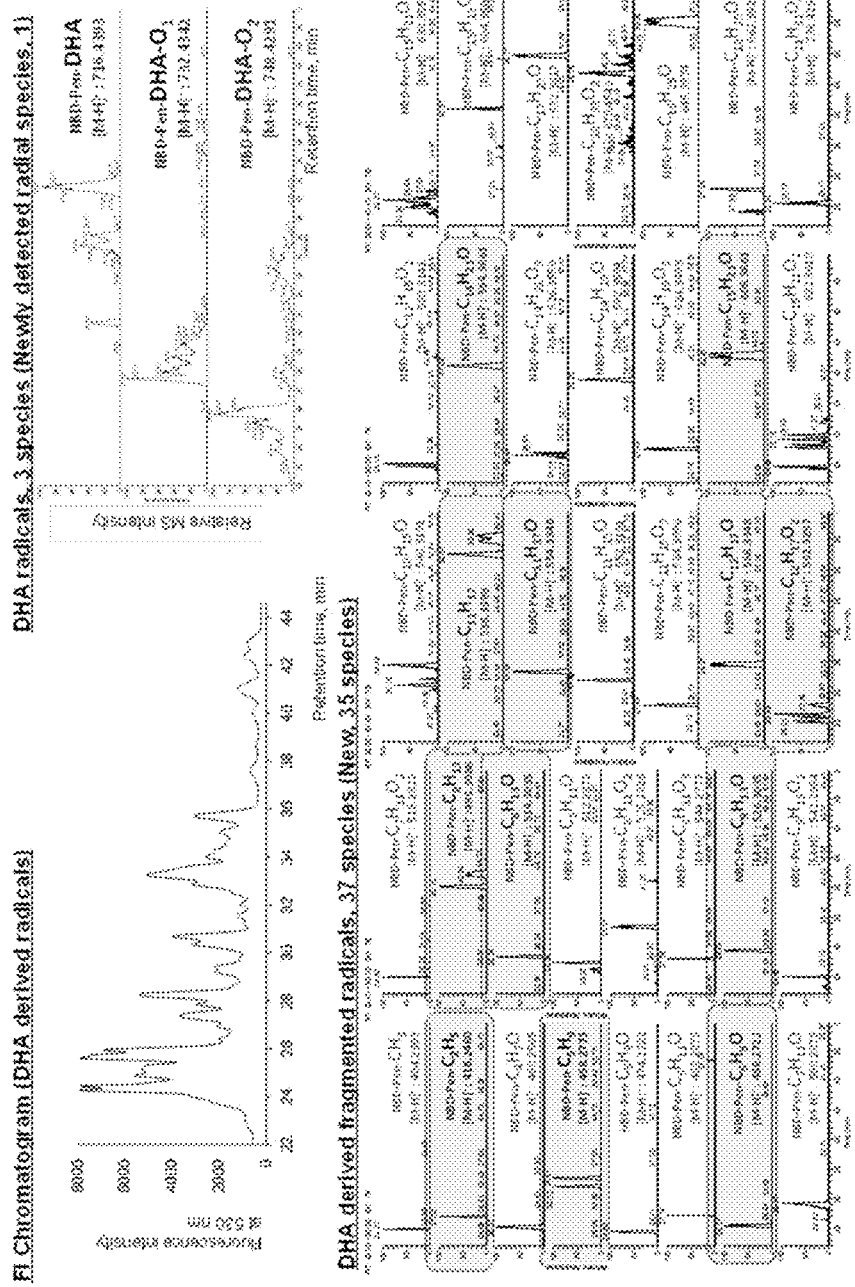
[Figure 10]

[Figure 11]
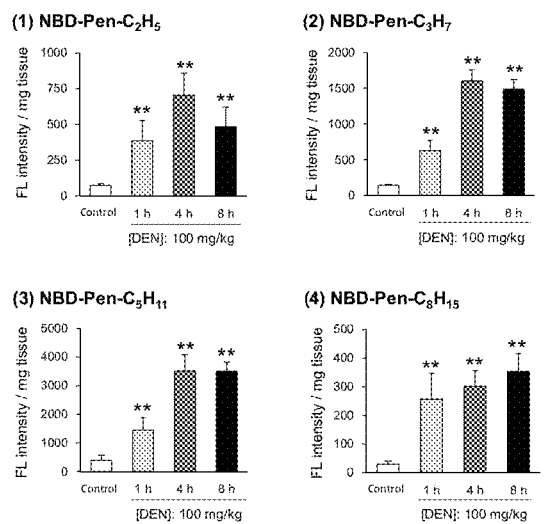
Mean ± S.D., n=3, *p<0.05, ** p<0.01 vs Control

METHOD FOR DETECTING A RADICAL COMPOUND DERIVED FROM A LIPID AND A COMPOUND DERIVED FROM THE RADICAL COMPOUND

TECHNICAL FIELD

The present invention provides a method for analyzing a structure of a lipid radical.

BACKGROUND ART

Genomic analysis targeting functions of genomes and genes, and proteome analysis targeting structures and functions of proteins have been actively carried out. Database of the obtained information contributes to elucidate a variety of phenomena including diseases in a living body.

Importance of lipidome analysis targeting functions and structures of lipids has been attractive. Nevertheless, since lipids are not genetically coded, insoluble in water, and the like, detection techniques are poor, research on lipids is still under development. However, since a large number of pharmaceuticals targeting a lipid such as indomethacin and statin have been developed, when a database on lipids is created, drug discovery research is expected to be accelerated.

Recently, it is revealed that reactive oxygen species (ROS) such as a superoxide anion radical, a hydroxy radical, a hydrogen peroxide and a singlet oxygen affect a variety of phenomena in a living body and that among them, a hydroxy radical has extremely high reactivity to cause various diseases. Studies are intensively carried out on them. It is known that such a hydroxy radical acts on lipids to produce lipid radicals.

Since a lipid radical is highly reactive and is unstable, once a lipid radical generates, a lipid peroxidation chain reaction occurs to produce peroxidized lipids, in turn, electrophilic compounds are produced as metabolites. Since lipids contain a lot of unsaturated fatty acids and hydrogen atoms of active methylene moieties thereof are extracted, they are susceptible to free radical attacks to induce lipid peroxidation chain reaction consisting of steps represented by the following reaction formulas (a)-(c) (FIG. 1).

[Equation 1]

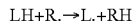  (a)

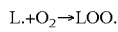  (b)

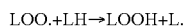  (c)

A free radical (R.) extracts a hydrogen atom from an unsaturated fatty acid (LH) to initiate a chain reaction (a); the produced lipid radical (L.) and an oxygen molecule react to produce a lipid peroxyl radical (LOO.) (b); and the lipid peroxyl radical extracts a hydrogen atom from unsaturated fatty acids around to produce a lipid peroxide (LOOH) and a lipid radical (L.) (c). The reproduced lipid radical (L.) initiates the second chain reaction cycle.

Lipid peroxides (LOOH) are converted into more than hundreds of electrophilic compounds, as metabolites thereof, such as malondialdehyde, 4-hydroxy-2-nonenal, acrolein, propanal, glyoxal and the like. It is known that these metabolites themselves or complexes produced with proteins respectively have cytotoxicity, inflammation, mutagenicity.

RELATED ARTS

Non-Patent Literature

Non-patent literature 1: Hollyfield J G. et al., Nat. Med., 14:194, 2008
Non-patent literature 2: Schutt F. et al. Invest. Ophthalmol. Vis. Sci., 44:3663, 2003
Non-patent literature 3: Verna L, et al., Pharmacol. Ther., 71:57, 1996
Non-patent literature 4: Park J E, et al., Cell, 140:197, 2010
Non-patent literature 5: Maeda S, et al., Cell, 121:977, 2005

SUMMARY OF THE INVENTION

Problem to be Solved by the Invention

For example, since a lot of unsaturated fatty acids are contained in a retina, and eyes are always exposed to sunshine, ROS generates a lot. As a result, a peroxidation reaction of fatty acids constitutively occurs in a retina. Actually, malondialdehyde, 4-hydroxy-2-nonenal, acrolein, propanal, glyoxal, etc. are detected as a peroxidized lipid and a metabolite thereof within a retina. Further, it is reported that a complex between these compounds and proteins may become causal substances for age-related macular degeneration (AMD) [Non-patent literature 1]. It is known that there are enormous kinds of such complexes and actually a very large number of molecules have been modified in a retina of AMD patients [Non-patent literature 2].

As above, only for AMD as an example, in order to prevent or treat it, its causal substances should be inhibited one by one, and, therefore, it cannot be a fundamental measure. Thus, the present inventors have first presumed AMD onset and progression routes, and summarized them systematically and comprehensively (FIG. 2).

Thereby, the present inventors have revealed that diseases caused from compounds produced in a series of reactions can be comprehensively prevented or treated by targeting lipid radicals which is precursors producing peroxidized lipids, instead of individual metabolites of peroxidized lipids.

Since the metabolites such as malondialdehyde, 4-hydroxy-2-nonenal, acrolein, propanal, glyoxal, etc. are stable compounds, structural analyses and functional researches on them are relatively easy. On the other hand, since lipid radicals are essentially unstable substances and, once they generate, they are immediately converted into lipid peroxyl radicals, peroxidized lipids, metabolites by chain reactions, it is substantially impossible to identify any lipid radicals.

Accordingly, in order to prevent or treat the respective lipid radical-inducible diseases, the present inventors challenged a problem to provide a method for scavenging unstable lipid-derived radicals and analyzing structures of those radicals.

Means for Solving the Problem

The present inventors found that when the fluorescent nitroxide 2,2,6-trimethyl-4-(4-nitrobenzo[1,2,5]oxadiazol-7-ylamino)-6-pentylpiperadine-1-oxyl (NBD-Pen) represented by the chemical structure (1):

[Chemical formula 1]

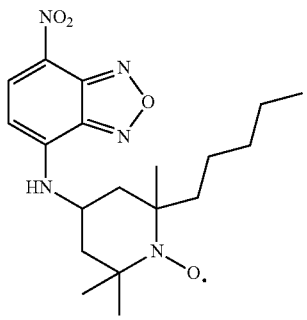

(1)

is applied to a living body subjected to oxidation stress, and analyzing a lipid extract extracted from the living body, a lipid radical or a radical of a fragmented lipid (fragment radical) can be scavenged and lipid-derived radicals contained in the lipid extract can be identified by combining fluorescent detection liquid chromatography (LC/FL) and mass spectrometry (MS).

Effect of the Invention

A combination of LC/FL/MS involving use of the fluorescent nitroxide can scavenge lipid radicals derived in a living body or fragment radicals thereof and to analyze their structures.

BRIEF EXPLANATION OF THE DRAWINGS

FIG. 1 A schematic chart of lipid peroxidation reactions.
FIG. 2 Age-related macular degeneration (AMD) onset and progression routes summarized by the present inventors.
FIG. 3 A graph showing reactivities of NBD-nitroxides with reactive oxygen species and lipid radicals.
FIG. 4 A graph showing reactivities of NBD-Pen with reactive oxygen species and lipid radicals.
FIG. 5 Graphs showing suppression of stimulus with lipid radicals by nitroxides.
FIG. 6 Schematic views showing suppression of hepatocellular carcinoma-induction with lipid radicals by nitroxides (a); and a graph showing the numbers of tumors (b).
FIG. 7 A schematic view of fluorescent detection of lipid radicals according to the present invention.
FIG. 8 A schematic diagram showing one embodiment of a LC/FL/MS system according to the present invention.
FIG. 9 Detection results of arachidonic acid (AA)-derived radical compound produced by AAPH stimulation.
FIG. 10 Detection results of docosahexaenoic acid (DHA)-derived radical compound produced by AAPH stimulation.
FIG. 11 Detection results of radical compound induced within a hepatocellular carcinoma model mouse by using NBD-Pen.

MODE FOR CARRYING OUT THE INVENTION

Reference Example 1: Development of Fluorescent Nitroxide

The present inventors developed a novel method of synthesizing a 2,6-substituted TEMPO-based nitroxide 2,2,6,6-tetramethylpiperadine-N-oxyl represented by the chemical structure (2):

[Chemical formula 2]

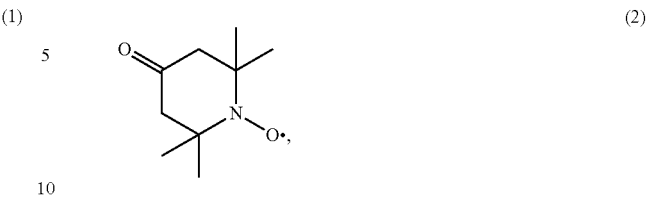

(2)

and found that an alkyl group is introduced in the vicinity of a radical part to enhance lipid affinity and an ability of suppressing lipid peroxidation and, then, lipid radicals can be effectively scavenged.

Additionally, the nitroxide (NO.) is a stable radical having paramagnetism and a property of decaying fluorescence by intersystem crossing due to photoinduced electron transfer and electron-spin exchange associating with charge separated states. A fluorescent nitroxide in which a fluorophore attaches to a nitroxide is in an intermolecular quenching state. However, it was confirmed that when the nitroxide reacted with a free radical to lose paramagnetism, it became a fluorescence emitting state. That is, the fluorescent nitroxide is useful as a probe to detect scavenging of lipid radicals by fluorometry.

The present inventors converted the carbonyl group at the 4th position into an amino group and covalently attached a fluorophore 7-nitrobenzofurazan (NBD) represented by the chemical structure (3):

[Chemical formula 3]

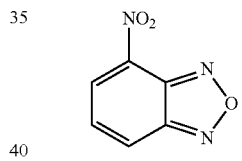

(3)

so as to make proximity with a radical moiety on the TEMPO-based nitroxide.

Most of lipid molecules to be detected exist within living body membrane to achieve a hydrophobic environment. Therefore, an environment-responsive fluorophore in which its fluorescence decays under hydrophilic environment and emits selectively high fluorescence under hydrophobic environment is best. For that reason, the present inventors chose NBD which widely used as a fluorophore in a lipid field such as phase transition and membrane fusion within a living body membrane or intercellular lipid metabolism and the like.

NBD derivatives are very useful to apply to imaging with a fluorescent microscopy because their excitation wavelength is around 470 nm which is suitable for argon laser excitation (488 nm). Further, since its emission maximum is around 530 nm, use of NBD derivatives is useful from the viewpoint of reducing autofluorescence from substances in a living body.

The present inventors found that introduction of a chain alkyl group in the vicinity of the radical moiety of TEMPO-based nitroxide changes the lipid affinity and steric hindrance of the compound and, thereby, lipid radicals can be effectively scavenged. For example, extending the alkyl chain at the $2^{nd}$ position (or the $6^{th}$ position) of nitroxide increased the lipid peroxidation suppressive ability.

The present inventors synthesized, as NBD-nitroxides with high lipid reactivity, Compound A (NBD-Me) and Compound B (NBD-Et) in which the $2^{nd}$ and $6^{th}$ positions were substituted, respectively, with two methyl groups or ethyl groups, and Compound C (NBD-Pen) in which the $2^{nd}$ position was substituted with two methyl groups and the $6^{th}$ position was substituted with pentyl group.

[Chemical formula 4]

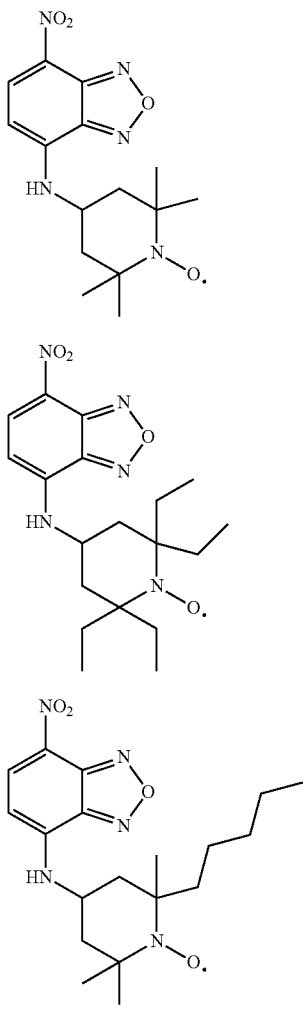

It was revealed that extension of one of the two alkyl groups attached to the $2^{nd}$ (or $6^{th}$) position increased the reactivity with the lipid radicals and that the complex of a nitroxide derivative and a lipid was thermally stable. That is, among Compounds A to C, Compound C: NBD-Pen was predominant.

Reference Example 2: Detection Sensitivity of Lipid Radical of NBD-Nitroxide (1) Reactivity of NBD-Nitroxide with Reactive Oxygen Species and Lipid Radicals In order to investigate reaction selectivities of the above three types of NBD-nitroxide (NBD-Me, NBD-Et and NBD-Pen), reactivities with various ROS and lipid radical were evaluated by fluorometry. When each NBD-nitroxide was reacted with hydrogen peroxide, hypochlorous acid, superoxide anion radical, hydroxy radical or nitric oxide, fluorescence did not increase much in any nitroxide. In addition, in the reaction with these compounds, no significant difference in fluorescence intensity was observed between these nitroxides, and there was no difference between the $2^{nd}$ and $6^{th}$ position substituents. On the other hand, it was revealed that when each NBD-nitroxide was reacted with lipid radical produced using lipoxygenase (LOX) for linoleic acid (LA), α-linolenic acid (ALA), or arachidonic acid (AA), its fluorescence intensity was significantly elevated, and lipid radical could be detected selectively and with high sensitivity. In particular, when NBD-Pen was used, it was found that the fluorescence intensity increased by about 10 to 26 times by reaction with lipid radical (FIG. 3).

(2) Reactivity of NBD-Pen with Reactive Oxygen Species and Lipid Radicals

For fluorescence detection of lipid radicals, the reactivity of the most sensitive NBD-Pen was further investigated.

When NBD-Pen was reacted with hydrogen peroxide, hypochlorous acid, superoxide anion radical or hydroxy radical, the same results as above were reproduced and the fluorescence did not increase much. On the other hand, when NBD-Pen was reacted with lipid radicals induced by activating LA, ALA, and AA, respectively, with any one of radical-inducing agents of lipoxygenase (LOX), 2,2'-azobis(2-methylpropion amidine) dihydrochoride (AAPH), and 2,2'-azobis(4-methoxy-2,4'-dimethylvaleronitorile (MeO-AMVN), the fluorescence intensity remarkably increased (FIG. 4).

Reference Example 3: Cytotoxicity of NBD-Nitroxide

Cytotoxicity of NBD-nitroxide was evaluated using human umbilical vein endothelial cell (HUVEC). When each concentration of the compound was added to HUVEC and the number of viable cells after incubation for 24 hours was counted, cytotoxicity was not observed up to 10 μM in any NBD-nitroxide.

Reference Example 4: Possibility of Hepatocellular Carcinogenesis with Lipid Radicals In addition, diethylnitrosamine (DEN) is metabolically activated by cytochrome P450 to produce a carbon centered radical. It is known that this radical alkylates a DNA and induces hepatocellular carcinoma [Non-patent literature 3].

[Chemical formula 5]

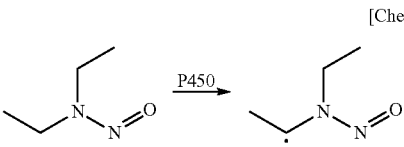

In a study on preparation of hepatocellular carcinoma model mice using DEN, it is already known that the carcinogenesis rate of obese mice is high [Non-patent literature 4], and that a large amount of ROS accumulates in a body of a hepatocellular carcinoma model mouse [Non-patent literature 5].

From the above two findings, the present inventors speculated that ROS activates a lipid and produces a lipid radical, and such a lipid radical also induces hepatocellular carcinoma.

The present inventors had confirmed that lipid radicals generated only 1 hour after administration of DEN in rats, but it was unknown whether the lipid radicals induced hepatocellular carcinoma.

Therefore, it was investigated whether inhibition of lipid radical generation affects hepatocellular carcinogenesis. The present inventors first synthesized Nitroxide compound D (4-hydroxy-2,2,6-trimethyl-6-pentylpiperidine-1-oxyl; OH-Pen) and Piperidine compound E (4-hydroxy-1-methoxy-2,2,6-trimethyl-6-pentylpiperidine-1-oxyl; OH-Pen-NOMe) lacking a lipid radical scavenging ability due to modification with a methyl group on the part of its nitroxide part of the nitroxide compound D. OH-Pen is a compound in which the fluorescent chromophore of NBD-Pen is unbound.

[Chemical formula 6]

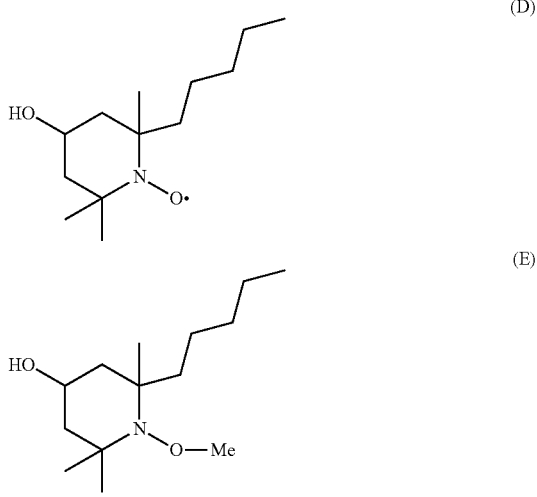

Six week-old male rats (F344) were divided into 4 groups, and as a control, rats in Group 1 were administered with saline (PBS) by intraperitoneal injection. Rats in Groups 2-4 were administered with DEN at 100 mg/kg by intraperitoneal injection.

One hour after DEN administration, physiological saline was administered to rats in Group 2 by intraperitoneal injection, rats in Group 3 were administered with a 500 μM OH-Pen solution at 4 ml/kg, and rats in Group 4 were administered with a 500 μM OH-Pen-NOMe solution at 4 ml/kg.

Twenty-four hours after DEN administration, livers were excised from rats in the respective groups and lipid extraction was carried out. For extracts, amounts of malondialdehyde; MDA as a peroxidized lipid marker, alanine transaminase (glutamate pyruvate transferase; ALT (GPT)) as a hepatic injury marker, and interleukin-6; IL-6 as an inflammatory marker were measured. The results are shown in FIG. 5.

As is apparent from the above results, as compared with the control (Group 1), each marker value increased by administration of DEN (Group 2), but when OH-Pen having lipid radical scavenging ability was administered, each marker value significantly decreased (Group 3). On the other hand, when OH-Pen-NOMe lacking lipid radical scavenging ability was administered, there was almost no drop in each marker value (Group 4).

Three months after DEN administration, rats in the respective groups were subjected to mixed anesthesia of 3 species, and they were sacrificed and livers were taken out promptly. Photographs of the livers taken from the rats of the respective groups are shown in FIG. 6, and the result of counting the number of tumor foci is shown in FIG. 6b.

As is clear from the above results, hepatocellular carcinoma was induced by DEN administration (Group 2), but administration of OH-Pen having a lipid radical scavenging ability suppressed hepatocellular carcinogenesis (Group 3). On the other hand, when OH-Pen-NOMe lacking a lipid radical scavenging ability was administered, hepatocellular carcinogenesis was not suppressed at all (Group 4).

Example 1

(1) Aim of the Experiments

In the reference example above, it was confirmed that NBD-Pen have a lipid radical scavenging ability, fluorescence sensitivity when a lipid radical is scavenged, nor cytotoxic at a concentration of 10 μM or less.

The present inventors predicted that NBD-nitroxide with a lipid radical scavenging ability could scavenge lipid radicals induced in the living body and its structure could be analyzed.

As mentioned above, it was found that lipids in living body become lipid radicals, and peroxidized lipids by chain reactions, and further metabolites and the like, and that they involved in diseases. Thus, if structural analysis would be possible on lipid radicals which have not been observed until now, it becomes possible to comprehensively analyze the relationship between lipids and its derivatives present in living body and diseases.

(2) In Vitro Scavenging of Lipid Radicals by NBD-Pen

The present inventors presumed that when NBD-Pen scavenges lipid radical (L.) and the radical adduct NBD-Pen-L is produced, fluorescence chromatogram and mass spectrometry may be combined to perform structural analysis of the scavenged lipid (LH).

For example, if three kinds of radical species respectively having $R_1$, $R_2$ or $R_3$ groups are contained in a sample, when liquid chromatogram of the sample to which NBD-Pen has been applied is observed by fluorometry, and fractions obtained at the respective column retention time is subject to mass analysis, the structures of $R_1$, $R_2$ and $R_3$ can be determined. A conceptual diagram of fluorescence detection of such a lipid radical according to the present invention is shown in FIG. 7.

In this Example, with 2,2'-azobis(2-methylpropion amidine) dihydrochloride (AAPH), lipid radicals were induced by activating linoleic acid (LA) and arachidonic acid (AA) as omega-6 fatty acid; and α-linolenic acid (ALA), eicosapentaenoic acid (EPA), and docosahexanoic acid (DHA) as omega-3 fatty acid.

An ethanol solution of each fatty acid 100 mM was prepared and diluted to a final concentration (500 μM) by adding a phosphate buffer solution thereto. To these fatty acid solutions, a 50 mM AAPH solution in phosphate buffer was added.

[Chemical formula 7]

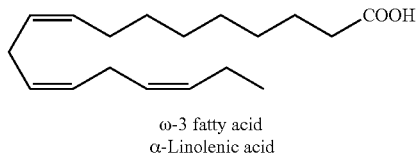

ω-3 fatty acid
α-Linolenic acid

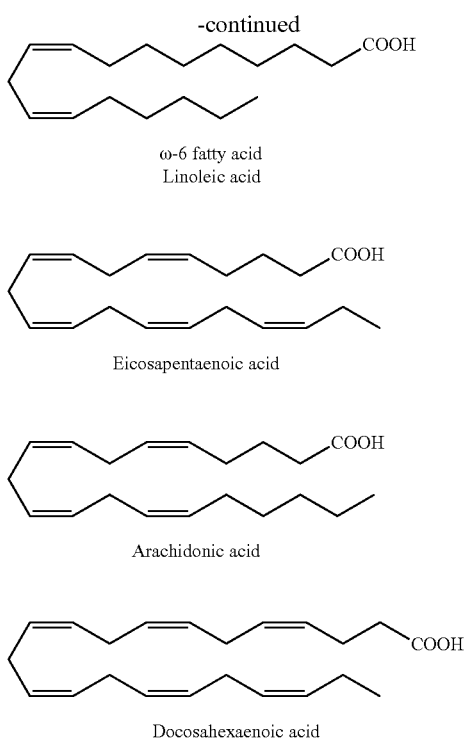

ω-6 fatty acid
Linoleic acid

Eicosapentaenoic acid

Arachidonic acid

Docosahexaenoic acid

By making NBD-Pen react with a solution in which lipid radicals are induced, a lipid was extracted from the reacted solution. The extract was analyzed using a LC/FL/MS system integrating fluorescence (FL) and mass spectrometer (MS) with high performance liquid chromatography (HPLC).

A schematic diagram showing one embodiment of a LC/FL/MS system according to the present invention is depicted in FIG. 8. A LC/FL/MS system 1 comprises a pump 11, a valve 12, a HPLC column 13, a fluorescence detector 14, a valve 15, an ion source for mass spectrometry 16, an ion detector for mass spectrometry 17, and a sampler 18 providing a sample via the valve 12 to the column 13. Additionally, a sample solution flowing out from the fluorescence detector may be disposed via the valve 15, when mass spectrometry is not performed.

It is appropriately selected according to the present invention, but not limited to, HPLC analysis is performed in this Example by injecting 10 μL of a sample solution into an InertSusteain® C18 analytical column (filled with ES silica having a particle size of 3 μm, 2.0×150 mm) manufactured by Mitsubishi Chemical Corporation, which is eluted with a mobile phase (A: 5.0 mM ammonium acetate in $H_2O$, B:ACN:$H_2O$ (95:5)) at 40° C. at a rate of 0.4 ml/min. The time program of mobile phase elution was set to B %: 0 to 22 min; 60%, 22 to 60 min; 80%, 60 to 70 min; 100%.

For each fraction eluted, fluorescence observation from NBD-Pen was performed at excitation wavelength (470 nm) and emission wavelength (530 nm) with a fluorescence detector (RF-20A xs manufactured by Shimadzu Corporation).

Next, each fraction thus obtained was introduced into an ion detector (Q Exactive™ Hibrid Quadrupole-Orbitrap™ MS manufactured by Thermo Fisher Scientific Co., Ltd.) by electrospray ionization (ESI) and subjected to mass spectrometry.

The structure of the radical adduct was analyzed by comparing the fluorescence peak observed at the LC/FL site with the precise mass analysis result at the column retention time.

Then, surprisingly, from the solution of docosahexaenoic acid (DHA) as omega-3 fatty acid, obtained were not only three adducts: an adduct in which arachidonic acid radical is attached to NBD-Pen (NBD-Pen-AA); an adduct in which one oxygen molecule is attached to that (NBD-Pen-AA-O1); and an adduct in which two oxygen molecules are attached (NBD-Pen-AA-O2), and also 25 types of adducts including adducts in which each of species $.C_5H_{11}$, $.C_8H_{15}$, $.C_7H_{13}O$ is attached to NBD-Pen, wherein 23 types out of which were novel adducts (FIG. 9).

In addition, from the solution of arachidonic acid (AA) as omega-6 fatty acid, obtained were not only three adducts: an adduct in which docosahexaenoic acid radical is attached to NBD-Pen (NBD-Pen-DHA); an adduct in which one oxygen molecule is attached to that (NBD-Pen-DHA-O1); and an adduct in which two oxygen molecules are attached (NBD-Pen-DHA-O2) and also 37 types of adducts including adducts in which each of species $.C_5H_9$, $.C_4H_7O$, $.C_7H_{11}O$ is attached to NBD-Pen, wherein 35 types out of which were novel adducts (FIG. 10).

Table 1 summarizes radical compound constituting radical adducts derived from the respective lipids: LA (18:2n-6), AA (20:4n-6), ALA (18:3n-3), EPA (20:5n-3) and DHA (22:6n-3) obtained by the method of the present invention.

As used herein, the term "radical compound" means a radical of a lipid itself (lipid radical) and a radical of a fragmented lipid (fragment lipid radical). Additionally, adducts in which radical compound are respectively attached to NBD-nitroxides (NBD-Me, NBD-Et, NBD-Pen):

[Chemical formula 8]

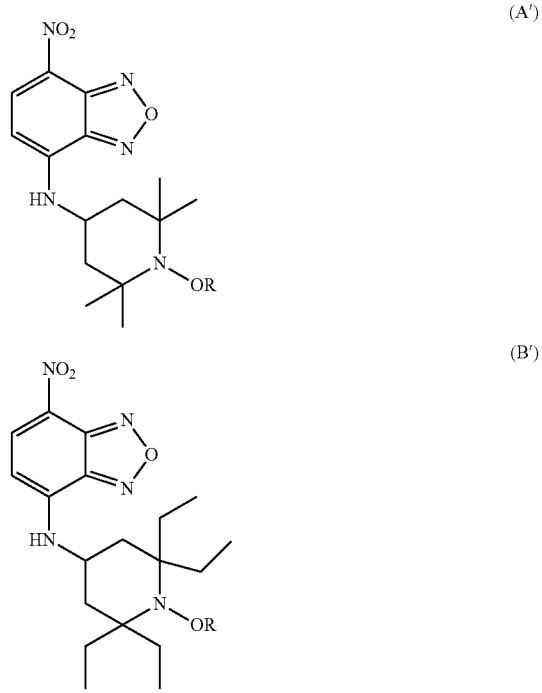

-continued (C')

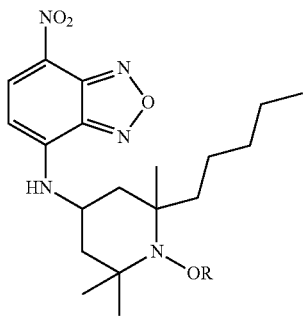

are collectively mentioned as "NBD-nitroxide R (NBD-Me-R, NBD-Et-R, NBD-Pen-R)", for example, an adduct in which a lipid radical is attached to NBD-Pen may be mentioned as "NBD-Pen-L".

TABLE 1

| Lipid | Radical compound |
|---|---|
| | ω-6 |
| LA | •LA, •LA-$O_1$, •LA-$O_2$<br>•$CH_3$, •$C_2H_5$, •$C_3H_7$, •$C_4H_9$, •$C_5H_{11}$, •$C_6H_{13}$, •$C_7H_{13}$, •$C_7H_{13}O$, •$C_8H_{15}$, •$C_8H_{15}O$,<br>•$C_9H_{15}$, •$C_9H_{15}O_2$, •$C_9H_{13}O_3$, •$C_{10}H_{17}O$, •$C_{11}H_{19}O_2$, •$C_{12}H_{21}O_2$ |
| AA | •AA, •AA-$O_1$, •$AA-O_2$,<br>•$CH_3$, •$C_2H_5$, •$C_3H_7$, •$C_4H_9$, •$C_5H_{11}$, •$C_6H_{13}$, •$C_6H_9O_3$, •$C_7H_{13}$, •$C_7H_{13}O$, •$C_8H_{15}$,<br>•$C_8H_{13}O_2$, •$C_8H_{15}O$, •$C_9H_{17}$, •$C_9H_{15}O_2$, •$C_9H_{13}O_3$, •$C_{10}H_{17}O$, •$C_{11}H_{10}$, •$C_{11}H_{17}O$,<br>•$C_{11}H_{19}O$, •$C_{11}H_{19}O_2$, •$C_{12}H_{19}O$, •$C_{12}H_{19}O_2$, •$C_{13}H_{19}O_2$, •$C_{14}H_{21}O$, •$C_{14}H_{23}O$, •$C_{15}H_{23}O$ |
| | ω-3 |
| ALA | •ALA, •ALA-$O_1$, •$ALA-O_2$<br>•$CH_3$, •$C_2H_5$, •$C_5H_9$, •$C_5H_9O$, •$C_6H_9O$, •$C_6H_{11}O$, •$C_7H_{11}O$, •$C_8H_{13}$, •$C_8H_{11}O$,<br>•$C_8H_{11}O_3$, •$C_8H_{13}O$, •$C_9H_{13}O$, •$C_9H_{13}O_2$, •$C_{10}H_{15}O$, •$C_{11}H_{17}$, •$C_{11}H_{15}O$, •$C_{11}H_{17}O$,<br>•$C_{11}H_{15}O_3$, •$C_{15}H_{21}O_2$, •$C_{15}H_{21}O_3$ |
| EPA | •EPA, •EPA-$O_1$, •$EPA-O_2$<br>•$CH_3$, •$C_2H_5$, •$C_5H_9$, •$C_5H_9O$, •$C_6H_9O$, •$C_6H_{11}O$, •$C_7H_{11}O$, •$C_8H_{13}$, •$C_8H_{11}O$,<br>•$C_8H_{11}O_3$, •$C_9H_{13}O$, •$C_9H_{13}O$, •$C_9H_{13}O_2$, •$C_{10}H_{15}O$, •$C_{11}H_{17}$, •$C_{11}H_{15}O$, •$C_{11}H_{17}O$,<br>•$C_{11}H_{15}O_3$, •$C_{12}H_{17}O$, •$C_{12}H_{17}O_2$, •$C_{14}H_{21}O$, •$C_{14}H_{19}O$, •$C_{15}H_{21}O$, •$C_{15}H_{21}O_2$, •$C_{15}H_{21}O_3$,<br>•$C_{17}H_{23}O$, •$C_{18}H_{25}O$ |
| DHA | •DHA, •DHA-O, •$DHA-O_2$,<br>•$CH_3$, •$C_2H_5$, •$C_5H_9$, •$C_5H_9O$, •$C_6H_9O$, •$C_6H_{11}O$, •$C_7H_{11}O$, •$C_8H_{13}$, •$C_8H_{11}O$,<br>•$C_8H_{11}O_3$, •$C_8H_{13}O$, •$C_9H_{13}O$, •$C_9H_{13}O_2$, •$C_{10}H_{15}O$, •$C_{11}H_{17}$, •$C_{11}H_{15}O$, •$C_{11}H_{17}O$,<br>•$C_{11}H_{15}O_3$, •$C_{12}H_{17}O$, •$C_{12}H_{17}O_2$, •$C_{14}H_{21}O$, •$C_{14}H_{19}O$, •$C_{15}H_{21}O$, •$C_{15}H_{21}O_2$, •$C_{15}H_{21}O_3$,<br>•$C_{17}H_{23}O$, •$C_{18}H_{25}O$, •$C_{21}H_{31}O_4$ |

*Radical compound newly found according to the present invention are shown in italics.

A LC/FL/MS analysis involving use of NBD-Pen was performed on linoleic acid (LA) radical-induced with AAPH to newly obtained compounds represented by NBD-Pen-R, wherein R is selected from a group consisting of $CH_3$, $C_2H_5$, $C_3H_7$, $C_4H_9$, $C_6H_{13}$, $C_7H_{13}$, $C_7H_{13}O$, $C_8H_{15}O$, $C_9H_{15}$, $C_9H_{15}O_2$, $C_9H_{13}O_3$, $C_{10}H_{17}O$, $C_{11}H_{19}O_2$, and $C_{12}H_{21}O_2$.

A LC/FL/MS analysis involving use of NBD-Pen was performed on arachidonic acid (AA) radical-induced with AAPH to newly obtained compounds represented by NBD-Pen-R, wherein R is selected from a group consisting of AA-$O_2$, $CH_3$, $C_2H_5$, $C_3H_7$, $C_4H_9$, $C_6H_{13}$, $C_6H_9O_3$, $C_7H_{13}$, $C_7H_{13}O$, $C_9H_3O_2$, $C_9H_{15}O$, $C_{91317}$, $C_9H_{15}O_2$, $C_9H_{13}O_3$, $C_{10}H_{17}O$, $C_{11}H_{19}$, $C_{11}H_{17}O$, $C_{11}H_{19}O$, $C_{11}H_{19}O_2$, $C_{12}H_{19}O$, $C_{12}H_{19}O_2$, $C_{13}H_{19}O_2$, $C_{14}H_{21}O$, $C_{14}H_{23}O$, and $C_{15}H_{23}O$.

A LC/FL/MS analysis involving use of NBD-Pen was performed on α-linolenic acid (ALA) radical-induced with AAPH to newly obtained compounds represented by NBD-Pen-R, wherein R is selected from a group consisting of ALA-$O_2$, $CH_3$, $C_5H_9O$, $C_6H_9O$, $C_6H_{11}O$, $C_7H_{11}O$, $C_8H_{13}$, $C_8H_{11}O$, $C_9H_{11}O_3$, $C_8H_{13}O$, $C_{91}H_3O$, $C_9H_{13}O_2$, $C_{10}H_{15}O$, $C_{11}H_{17}$, $C_{11}H_{15}O$, $C_{11}H_{17}O$, $C_{11}H_{15}O_3$, $C_{15}H_{21}O_2$, and $H_{21}O_3$.

A LC/FL/MS analysis involving use of NBD-Pen was performed on eicosapentaenoic acid (EPA) radical-induced with AAPH to newly obtained compounds represented by NBD-Pen-R, wherein R is selected from a group consisting of EPA-$O_2$, $CH_3$, $C_5H_9O$, $C_6H_9O$, $C_6H_{11}O$, $C_7H_{11}O$, $C_8H_{13}$, $C_8H_{11}O$, $C_8H_{11}O_3$, $C_8H_{13}O$, $C_9H_{13}O$, $C_9H_{13}O_2$, $C_{10}H_{15}O$, $C_{11}H_{17}$, $C_{11}H_{15}O$, $C_{11}H_{17}O$, $C_{11}H_{15}O_3$, $C_{12}H_{17}O$, $C_{12}H_{17}O_2$, $C_{14}H_{21}O$, $C_{14}H_{19}O$, $C_{15}H_{21}O$, $C_{15}H_{21}O_2$, $C_{15}H_{21}O_3$, $C_{17}H_{23}O$, and $C_{18}H_{25}O$.

A LC/FL/MS analysis involving use of NBD-Pen was performed on docosahexaenoic acid (DHA) radical-induced with AAPH to newly obtained compounds represented by NBD-Pen-R, wherein R is selected from a group consisting of DHA-$O_2$, $CH_3$, $C_5H_9O$, $C_6H_9O$, $C_6H_{11}O$, $C_7H_{11}O$, $C_8H_{13}$, $C_8H_{11}O$, $C_8H_{11}O_3$, $C_8H_{13}O$, $C_9H_3O$, $C_9H_{13}O_2$, $C_{10}H_{15}O$, $C_{11}H_{17}$, $C_{11}H_{15}O$, $C_{11}H_{17}O$, $C_{11}H_{15}O_3$, $C_{12}H_{17}O$, $C_{12}H_{17}O_2$, $C_{14}H_{21}O$, $C_{14}H_{19}O$, $C_{15}H_{21}O$, $C_{15}H_{21}O_2$, $C_{15}H_{21}O_3$, $C_{17}H_{23}O$, $C_{18}H_{25}O$, and $C_2H_{31}O_4$.

Additional analysis revealed that as R of the compounds whose structure was determined for omega-3 fatty acid, at least $C_5H_9$, $C_5H_9O$, $C_6H_9O$, $C_6H_{11}O$, $C_7H_{11}O$, $C_8H_{13}$, $C_8H_{11}O$, $C_8H_{11}O_3$, $C_{10}H_{15}O$, $C_{11}H_{17}$, $C_{11}H_{15}O$, and $C_{11}H_{17}O$ are common; as R of the compounds whose structure was determined for omega-6 fatty acid, at least $C_5H_{11}$, $C_6H_{13}$, $C_7H_{13}$, $C_7H_{13}O$, $C_8H_{15}$, $C_8H_{15}O$, $C_9H_{15}$, and $C_{10}H_{17}O$ are common; and the common structure for omega-3 fatty acid and that for omega-6 fatty acid are different from each other.

Further, among omega-6 fatty acid, at least $C_8H_5$, $C_8H_{15}O$, $C_{11}H_{19}$, $C_{11}H_{17}O$, $C_{11}H_{19}O$, $C_{11}H_{19}O_2$, $C_{12}H_9O$, $C_{12}H_9O_2$, $C_{12}H_{19}O_2$, $C_{13}H_{19}O_2$, $C_{14}H_{21}O$, $C_{14}H_{23}O$, $C_{15}H_{23}O$ as R of the compounds whose structure was specified per arachidonic acid (AA) were found to be different from those of the compounds whose structure was specified for linoleic acid (LA).

Example 2

(1) Aim of Experiment

Example 1 suggests that, with a LC/FL/MS analysis using NBD-Pen, based on the combination of obtained radical compounds, fatty acids contained in an unknown sample can be identified.

Therefore, radical compounds produced in a living body of a mouse were detected with a LC/FL/MS analysis using NBD-Pen.

(2) Scavenging of Lipid Radicals Induced in Hepatocellular Carcinoma Model Mouse by NBD-Pen Male mice (C57BL/6J) at 8 weeks of age were divided into two groups. As a control, physiological saline (PBS) was administered to mice in Group 1 by intraperitoneal injection. DEN at 100 mg/kg was administered to mice in Group 2 by intraperitoneal injection.

Four hours after DEN administration, a 500 μM NBD-Pen solution was administered at 4 ml/kg to mice in Groups 1 and 2 by intraperitoneal injection.

Fifteen minutes after administration of NBD-Pen, livers were excised from the mice in the respective groups and lipid extraction was performed. LC/FL/MS analysis was performed on extracts under the same conditions as in Example 1. The structure of the radical adduct was analyzed by comparing the fluorescence peak observed at the LC/FL site with the precise mass analysis result at that column retention time. The results are described in Table 2 and FIG. 11.

TABLE 2

| Hepatocellular carcinoma inducing agent | Lipid radical scavenger | Fluorescent intensity of NBD-Pen-R (a.u.) R | | | |
|---|---|---|---|---|---|
| | | $C_2H_5$ | $C_3H_7$ | $C_5H_{11}$ | $C_5H_{15}$ |
| Gr. 1 | — | NBD-Pen | 72.95 | 143.69 | 393.38 | 29.72 |
| Gr. 2 | DEN | NBD-Pen | 704.15 | 1604.07 | 3511.72 | 353.94 |

Since NBD-Pen-$C_5H_{11}$, which is an identification marker for omega-6 fatty acid and, further NBD-Pen-$C_8H_{15}$ were detected as understood from Table 2, generation of arachidonic acid (AA) was verified.

INDUSTRIAL AVAILABILITY

By using the fluorescent nitroxide according to the present invention, lipid-derived radicals induced with reactive oxygen species (ROS) in a living body can be scavenged to determine the radical structures thereof. By this method, it is possible to elucidate the relevance to diseases caused by lipid radicals such as age-related macular degeneration and hepatocellular carcinoma.

EXPLANATION FOR SIGNS

1 LC/FL/MS system
11 Pump
12 Valve
13 Liquid chromatography column
14 Fluorescence detector
15 Valve
16 Ion source for mass spectrometry
17 Ion detector for mass spectrometry
18 Sampler

The invention claimed is:

1. A compound, which is the following compound (C'):

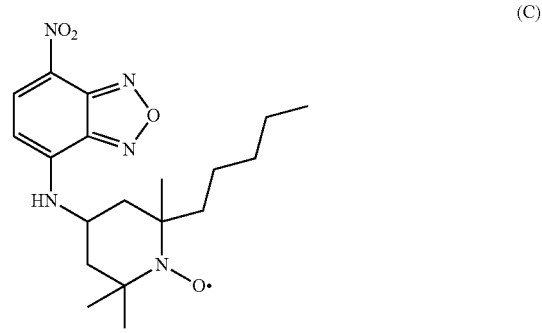

(C)

wherein

R is selected from a group consisting of $CH_3$, $C_2H_5$, $C_3H_7$, $C_4H_9$, $C_6H_{13}$, $C_7H_{13}$, $C_7H_{13}O$, $C_8H_{15}O$, $C_9H_{15}$, $C_9H_{15}O_2$, $C_9H_{13}O_3$, $C_{10}H_{17}O$, $C_{11}H_{19}O_2$, and $C_{12}H_{21}O_2$; or R is selected from a group consisting of AA-$O_2$, $CH_3$, $C_2H_5$, $C_3H_7$, $C_4H_9$, $C_6H_{13}$, $C_6H_9O_3$, $C_7H_{13}$, $C_7H_{13}O$, $C_8H_{13}O_2$, $C_8H_{15}O$, $C_9H_{17}$, $C_9H_{15}O_2$, $C_9H_{13}O_3$, $C_{10}H_{17}O$, $C_{11}H_{19}$, $C_{11}H_{17}O$, $C_{11}H_{19}O$, $C_{11}H_{19}O_2$, $C_{12}H_{19}O$, $C_{12}H_{19}O_2$, $C_{13}H_{19}O_2$, $C_{14}H_{21}O$, $C_{14}H_{23}O$, and $C_{15}H_{23}O$, and wherein AA represents arachidonic acid; or R is selected from a group consisting of ALA-$O_2$, $CH_3$, $C_5H_9O$, $C_6H_9O$, $C_6H_{11}O$, $C_7H_{11}O$, $C_8H_{13}$, $C_8H_{11}O$, $C_8H_{11}O_3$, $C_8H_{13}O$, $C_9H_{13}O$, $C_9H_{13}O_2$, $C_{10}H_{15}O$, $C_{11}H_{17}$, $C_{11}H_{15}O$, $C_{11}H_{17}O$, $C_{11}H_{15}O_3$, $C_{15}H_{21}O_2$, and $C_{15}H_{21}O_3$ and, wherein ALA represents α-linolenic acid; or R is selected from a group consisting of EPA-$O_2$, $CH_3$, $C_5H_9O$, $C_6H_9O$, $C_6H_{11}O$, $C_7H_{11}O$, $C_8H_{13}$, $C_8H_{11}O$, $C_8H_{11}O_3$, $C_8H_{13}O$, $C_9H_{13}O$, $C_9H_{13}O_2$, $C_{10}H_{15}O$, $C_{11}H_{17}$, $C_{11}H_{15}O$, $C_{11}H_{17}O$, $C_{11}H_{15}O_3$, $C_{12}H_{17}O$, $C_{12}H_{17}O_2$, $C_{14}H_{21}O$, $C_{14}H_{19}O$, $C_{15}H_{21}O$, $C_{15}H_{21}O_2$, $C_{15}H_{21}O_3$, $C_{17}H_{23}O$, and $C_{18}H_{25}O$ and, wherein EPA represents eicosapentaenoic acid; or R is selected from a group consisting of DHA-$O_2$, $CH_3$, $C_5H_9O$, $C_6H_9O$, $C_6H_{11}O$, $C_7H_{11}O$, $C_8H_{13}$, $C_8H_{11}O$, $C_8H_{11}O_3$, $C_8H_{13}O$, $C_9H_{13}O$, $C_9H_{13}O_2$, $C_{10}H_{15}O$, $C_{11}H_{17}$, $C_{11}H_{15}O$, $C_{11}H_{17}O$, $C_{11}H_{15}O_3$, $C_{12}H_{17}O$, $C_{12}H_{17}O_2$, $C_{14}H_{21}O$, $C_{14}H_{19}O$, $C_{15}H_{21}O$, $C_{15}H_{21}O_2$, $C_{15}H_{21}O_3$, $C_{17}H_{23}O$, $C_{18}H_{25}O$, and $C_{21}H_{31}O_4$ and, wherein DHA represents docosahexaenoic acid.

2. The compound of claim 1, wherein

R is selected from a group consisting of $C_7H_{13}$, $C_7H_{13}O$, $C_8H_{15}O$, $C_9H_{15}$, $C_9H_{15}O_2$, $C_9H_{13}O_3$, $C_{10}H_{17}O$, $C_{11}H_{19}O_2$, and $C_{12}H_{21}O_2$; or R is selected from a group consisting of AA-$O_2$, $C_6H_9O_3$, $C_7H_{13}$, $C_7H_{13}O$, $C_8H_{13}O_2$, $C_8H_{15}O$, $C_9H_{17}$, $C_9H_{15}O_2$, $C_9H_{13}O_3$, $C_{10}H_{17}O$, $C_{11}H_{19}$, $C_{11}H_{17}O$, $C_{11}H_{19}O$, $C_{11}H_{19}O_2$, $C_{12}H_{19}O$, $C_{12}H_{19}O_2$, $C_{13}H_{19}O_2$, $C_{14}H_{21}O$, $C_{14}H_{23}O$, and $C_{15}H_{23}O$, and wherein AA represents arachidonic acid; or R is selected from a group consisting of ALA-$O_2$, $C_5H_9O$, $C_6H_9O$, $C_6H_{11}O$, $C_7H_{11}O$, $C_8H_{13}$, $C_8H_{11}O$, $C_8H_{11}O_3$, $C_8H_{13}O$, $C_9H_{13}O$, $C_9H_{13}O_2$, $C_{10}H_{15}O$, $C_{11}H_{17}$, $C_{11}H_{15}O$, $C_{11}H_{17}O$, $C_{11}H_{15}O_3$, $C_{15}H_{21}O_2$, and $C_{15}H_{21}O_3$ and, wherein ALA represents α-linolenic acid; or R is selected from a group consisting of EPA-$O_2$, $C_5H_9O$, $C_6H_9O$, $C_6H_{11}O$, $C_7H_{11}O$, $C_8H_{13}$, $C_5H_{11}O$, $C_8H_{11}O_3$, $C_8H_{13}O$, $C_9H_{13}O$, $C_9H_{13}O_2$, $C_{10}H_{15}O$, $C_{11}H_{17}$, $C_{11}H_{15}O$, $C_{11}H_{17}O$, $C_{11}H_{15}O_3$, $C_{12}H_{17}O$, $C_{12}H_{17}O_2$, $C_{14}H_{21}O$, $C_{14}H_{19}O$, $C_{15}H_{21}O$, $C_{15}H_{21}O_2$, $C_{15}H_{21}O_3$, $C_{17}H_{23}O$, and $C_{18}H_{25}O$ and, wherein EPA represents eicosapentaenoic acid; or R is selected from a group consisting of DHA-$O_2$, $C_5H_9O$, $C_6H_9O$, $C_6H_{11}O$, $C_7H_{11}O$, $C_8H_{13}$, $C_5H_{11}O$, $C_8H_{11}O_3$, $C_8H_{13}O$, $C_9H_{13}O$, $C_9H_{13}O_2$, $C_{10}H_{15}O$, $C_{11}H_{17}$, $C_{11}H_{15}O$, $C_{11}H_{17}O$, $C_{11}H_{15}O_3$, $C_{12}H_{17}O$, $C_{12}H_{17}O_2$, $C_{14}H_{21}O$, $C_{14}H_{19}O$, $C_{15}H_{21}O$, $C_{15}H_{21}O_2$, $C_{15}H_{21}O_3$, $C_{17}H_{23}O$, $C_{18}H_{25}O$, and $C_{21}H_{31}O_4$ and, wherein DHA represents docosahexaenoic acid.

* * * * *